United States Patent [19]

Olsen et al.

[11] Patent Number: 5,562,710

[45] Date of Patent: Oct. 8, 1996

[54] DEFIBRILLATOR PATIENT CONNECTION SYSTEM WITH AUTOMATIC IDENTIFICATION

[75] Inventors: Kurt F. Olsen, McMinnville, Oreg.; Phillip H. Salvatori, N. Andover, Mass.; Daniel J. Powers, McMinnville, Oreg.

[73] Assignee: Hewlett-Packard Company, Palo Alto, Calif.

[21] Appl. No.: 437,119

[22] Filed: May 5, 1995

Related U.S. Application Data

[62] Division of Ser. No. 43,421, Apr. 6, 1993, Pat. No. 5,441,520.

[51] Int. Cl.$^6$ ........................................... A61N 1/39
[52] U.S. Cl. ..................... 607/5; 607/63; 607/115; 439/909
[58] Field of Search ..................... 607/1, 2, 5, 63, 607/115; 439/909

[56] References Cited

U.S. PATENT DOCUMENTS

| | | | |
|---|---|---|---|
| 4,202,351 | 5/1980 | Biche | 128/696 |
| 4,681,112 | 7/1987 | Jones et al. | 607/5 |
| 4,785,812 | 11/1988 | Pihl et al. | 128/734 |
| 4,964,407 | 10/1990 | Baker, Jr. et al. | 607/27 |
| 5,078,615 | 1/1992 | Bensen et al. | 607/5 |
| 5,105,821 | 4/1992 | Reyes | 607/5 |
| 5,233,986 | 8/1993 | Robson | 607/27 |

*Primary Examiner*—William E. Kamm
*Assistant Examiner*—Kennedy J. Schaetzle

[57] ABSTRACT

A defibrillator patient connection system is disclosed for automatically identifying to a defibrillator system the type of pads or paddles assembly connected to the system for conveying electrical energy to shock a patient. Each of the available pads or paddles assemblies is identified by a corresponding analog voltage level provided to the base unit through a corresponding cable assembly. The identification voltage is sensed by an A/D converter in the defibrillator base unit. The identification voltage is provided to the base unit on a charge-done signal line which otherwise is asserted by the base unit to controllably actuate a charge-done indicator light in an external paddles assembly. The disclosed methods and apparatus thus maintain a simple defibrillator/cable assembly interface and require no additional signal lines for implementing automatic identification. A plug assembly latch mechanism also is disclosed that provides the dual functions of locking a plug assembly in place in the defibrillator base unit and preventing actuation of discharge buttons on the plug assembly when the latch is not in the locked position, thereby avoiding a high energy discharge unless the plug assembly is securely locked in position.

5 Claims, 4 Drawing Sheets

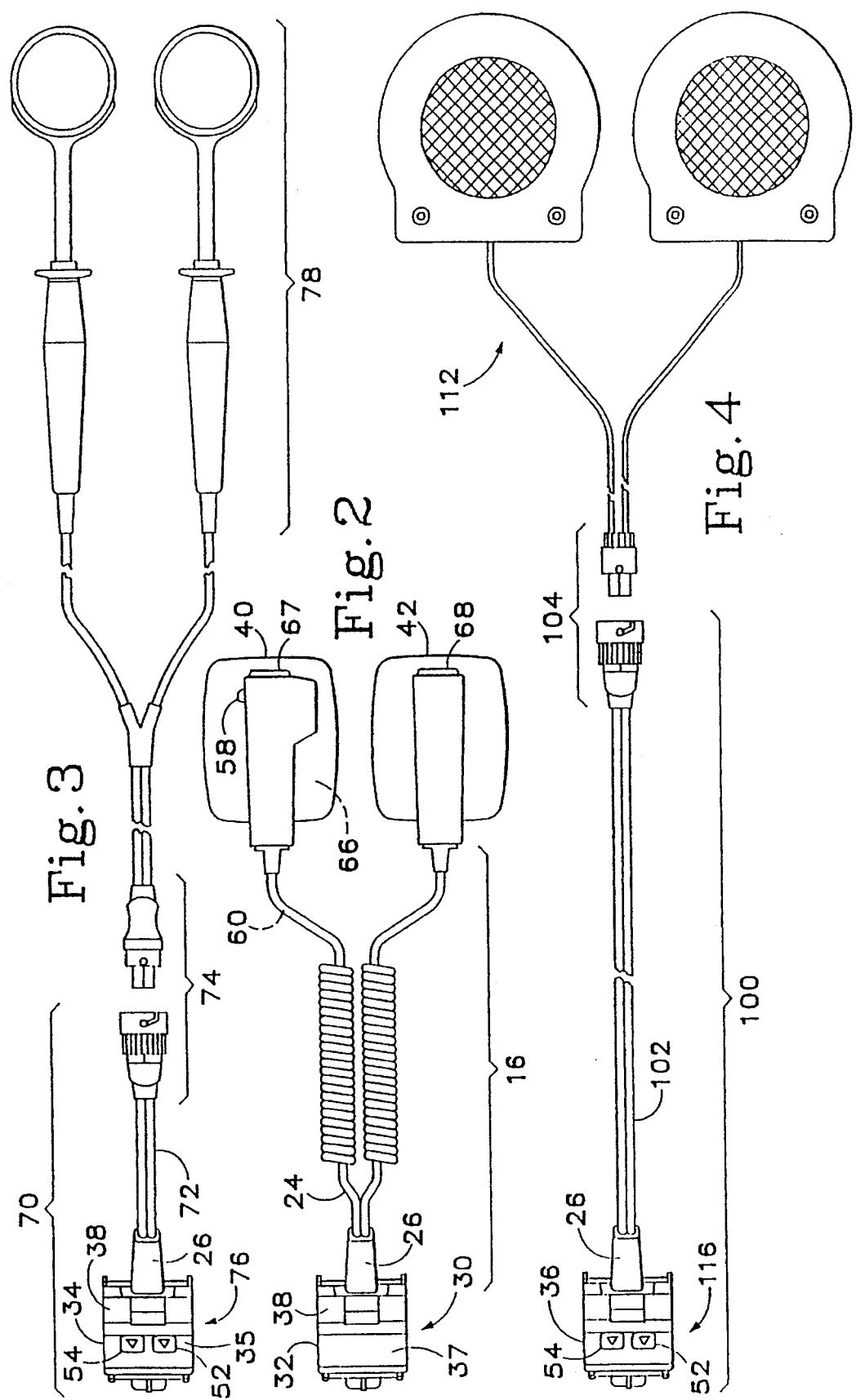

DEFIBRILLATOR PATIENT CONNECTION SYSTEM WITH AUTOMATIC IDENTIFICATION

This is a divisional of application Ser. No. 08/043,421 filed on Apr. 6, 1993, now U.S. Pat. No. 5,441,520.

BACKGROUND OF THE INVENTION

Defibrillator systems provide measured amounts of electrical energy for shocking a cardiac patient. A defibrillator system also typically includes ECG monitoring apparatus. ECG data acquired by the monitoring apparatus may be displayed for example on a CRT built into the defibrillator unit and/or recorded on hard copy or other data storage means. The ECG front end which is Used to acquire ECG data also may be used for triggering the defibrillator for synchronized cardioversion. The ECG front end can acquire ECG data from the patient either through external paddles, which also are used to administer a shock to the patient, or through a separate set of leads coupled to ECG electrodes.

Various pads or paddles may be connected, one at a time, to the defibrillator base unit for conveying electrical energy to the patient. However, it is essential for the defibrillator base unit to identify what type of pads or paddles are presently connected to it, as well as to detect when no pads or paddles are connected to the unit. The selected pads or paddles may be identified by the user, and the selection input to the base unit by setting a switch or pressing a button. This method, however, is subject to user error, and adds complexity to the user interface or keypanel. Moreover, this step adds to the setup time in an application where a patient's life may be in danger and, therefore, time is of the essence. It would be preferable to automatically identify the connected pads or paddles to the defibrillator base unit without operator input.

One way to automatically identify the selected paddle assembly is a binary encoding scheme in which two or more signal lines are used as bits to encode an identifying number. Two bits of data thus could be used to identify one of four types of pads or paddles, and three bits of data would identify one out of eight. Each pad or paddle assembly could include an identification circuit arranged to assert the various signal lines to logic hi or low levels according to the encoding scheme. A supply voltage and ground lines thus would also be required. However, it is desirable to minimize the number of such signal lines and thus keep the interface between the base unit and the various paddle assemblies as simple as possible.

Moreover, it is difficult if not impossible to provide electronic identification circuits in some types of paddles. For example, internal paddle assemblies (those that are used inside a patient's body during surgery) must be sterilizable. Any electronic circuitry required within the internal paddles assembly would have to be encapsulated in a sterilizable package at considerable cost and complexity of manufacture. In the case of adhesive pads, the pads are discarded rather than sterilized and reused, so their cost also is of particular concern. Accordingly, electronic circuitry for identifying the pads must be kept to a minimum or avoided entirely, if possible.

Accordingly, the need remains for a defibrillator patient connection system that automatically identifies a type of pads or paddles connected to a defibrillator base unit, while maintaining a simple interface between the base unit and the paddle assemblies, and keeping electronic circuitry to a minimum in certain types of paddles.

SUMMARY OF THE INVENTION

The present invention is directed to a defibrillator system, which includes a base unit to provide controlled amounts of electrical energy for shocking a cardiac patient, and at least two available types of pads or paddles for administering the electrical energy to the patient. We refer generally to the various pads and paddles available for this purpose as "administering means". The types of available administering means may include, for example, a pair of external paddle assemblies, a pair of internal paddle assemblies and a pair of adhesive pads (or "patient pads").

A corresponding cable assembly is provided for connecting each of the types of administering means to the base unit for use, and means are included for automatically identifying to the base unit the type of administering means connected to the base unit, or that no administering means is connected to the base unit when that is the case. It is desirable to disable high-energy charging circuits in the defibrillator when no pads or paddles are connected to the base unit for safety reasons.

Each of the various pads or paddle assemblies which may be connected to the base unit is identified in the base unit by a corresponding analog voltage level. This has the advantage of minimizing the number of electrical connections necessary for such identification. Circuitry for providing the corresponding identifying voltage level is disposed in the external paddles. In the cases of internal paddles or patient pads, appropriate provisions are made in the respective cable plug assemblies for providing a corresponding analog voltage level to the base unit for identification. Cable assemblies are mechanically keyed so as to prevent connecting patient pads to a plug assembly that contains circuitry for identifying internal paddles, and vice versa.

In all cases, a supply voltage is provided by the base unit. The supply voltage is carried to the external paddles circuitry via the corresponding cable assembly, where it is attenuated to form a predetermined identifying voltage level. In other cases, the corresponding identifying voltage is formed in the cable plug assembly, so that it need not be carried out to the pads or internal paddles.

In the preferred embodiment, the external paddles have an indicator light for indicating that the base unit has charged to a selected energy level ("charge done"). The external paddles cable assembly includes a "charge-done" signal line for carrying a charge-done signal from the base unit for controllably actuating the indicator light. A predetermined analog voltage level for identifying the external paddles is returned to the base unit via the charge-done signal line. The other administering means, i.e. the internal paddles and the patient pads, also are identified by applying the respective identifying voltage levels to the charge-done signal line, although in those cases this is done in the plug assembly. An analog to digital converter is used in the base unit for sensing the analog voltage level and inputting that information to the defibrillator processor or controller. Charge-done signal circuitry in the defibrillator base unit is arranged to provide a predetermined analog voltage level to the A/D circuit when no pads or paddles are connected to the base unit, thereby identifying that situation.

An object of the present invention is to automatically identify in a defibrillator base unit each of a plurality of different types of pads or paddles which may be connected to the base unit without adding signal lines to the defibrillator interface.

Another object of the invention is to provide for automatic identification of internal paddle assemblies, while maintaining their autoclavability.

A further object of the present invention is to use an existing signal line in the defibrillator interface for automatic identification of a type of paddles connected to the base unit.

Yet another object of the invention is to employ an analog voltage level applied to the charge-done signal line for identifying a pads or paddles assembly connected to the base unit.

The foregoing and other objects, features and advantages of the invention will become more readily apparent from the following detailed description of a preferred embodiment which proceeds with reference to the drawings.

BRIEF DESCRIPTION OF THE DRAWINGS

FIG. 2 illustrates a pair of external paddles and associated cable assembly for connecting the external paddles to the base unit.

FIG. 3 illustrates a pair of internal paddles and associated cable assembly for connecting the internal paddles to the base unit.

FIG. 4 illustrates a pair of patient pads and associated cable assembly for connecting the patient pads to the base unit.

FIG. 7 is a perspective view of a plug assembly engaged in a plug connector in the base unit with the plug assembly latch unlocked.

FIG. 8 is an enlarged, partially cutaway view of a portion of the apparatus of FIG. 7.

FIG. 9 is a perspective view of a plug assembly engaged in a plug connector in the base unit with the plug assembly latch locked.

FIG. 10 is an enlarged, partially cutaway view of a portion of the apparatus of FIG. 9.

DETAILED DESCRIPTION OF THE PREFERRED EMBODIMENT

Figure 1:
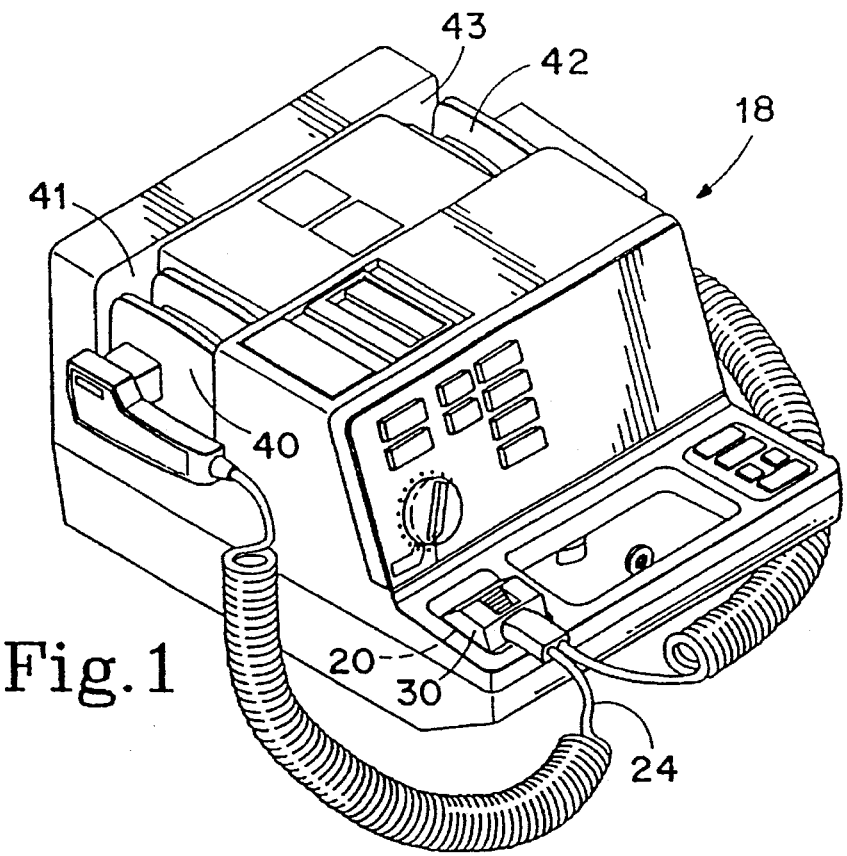
FIG. 1 is a perspective view of a defibrillator system base unit.

FIG. 1 is a perspective view of a defibrillator system of a type in which the present invention may be employed. The defibrillator system includes a base unit 18 for providing electrical energy to shock a patient. Various types of pads or paddle assemblies may be used with this system. In FIG. 1, external paddle assemblies 40, 42 are illustrated. The paddle assemblies are disposed in respective recesses 41, 43 which are provided in the base unit 18 for storing the external paddles when they are not in use. The paddles are connected to the base unit by a cable assembly which includes a cable 24 fixed to a plug assembly 30. The plug assembly 30 is shown engaged in the base unit as will be further described below.

Referring now to FIG. 2, the external paddles are illustrated in a top plan view, along with the associated cable assembly 16. Cable assembly 16 includes the plug assembly 30 and a pair of cables, for example cable 24, for connecting the paddle assemblies 40, 42 to the plug assembly. A strain relief interface 26, formed of a sturdy yet pliable material, is provided where the cable 24 enters the plug assembly. The plug assembly 30 and its interface with the base unit will be described further below, following a description of alternative types of pads and paddle assemblies.

FIG. 3 illustrates a pair of internal paddles 78, which may be connected to the base unit by means of an associated cable assembly 70. Cable assembly 70 includes a cable 72 fixed to a plug assembly 76. Plug assembly 76, like plug assembly 30, is arranged for interfitting engagement with a connector in the base unit. A coupler 74 is provided for removably connecting the internal paddles to the cable assembly 70.

FIG. 4 illustrates a pair of patient adhesive pads 112. The patient pads 112 may be connected to the base unit via an associated cable assembly 100. Cable assembly 100 includes a cable 102 fixed to a corresponding plug assembly 116. A pads coupler 104 is provided for connecting the patient pads to the cable assembly 100. Note that the patient pads coupler 104 is mechanically keyed differently (not shown) from the internal paddles coupler 74 shown in FIG. 3. This arrangement prevents connection of the internal paddles 78 to the patient pads cable assembly 100, and likewise prevents mechanical connection of the patient pads 112 to the internal paddles cable assembly 70.

Figure 5:
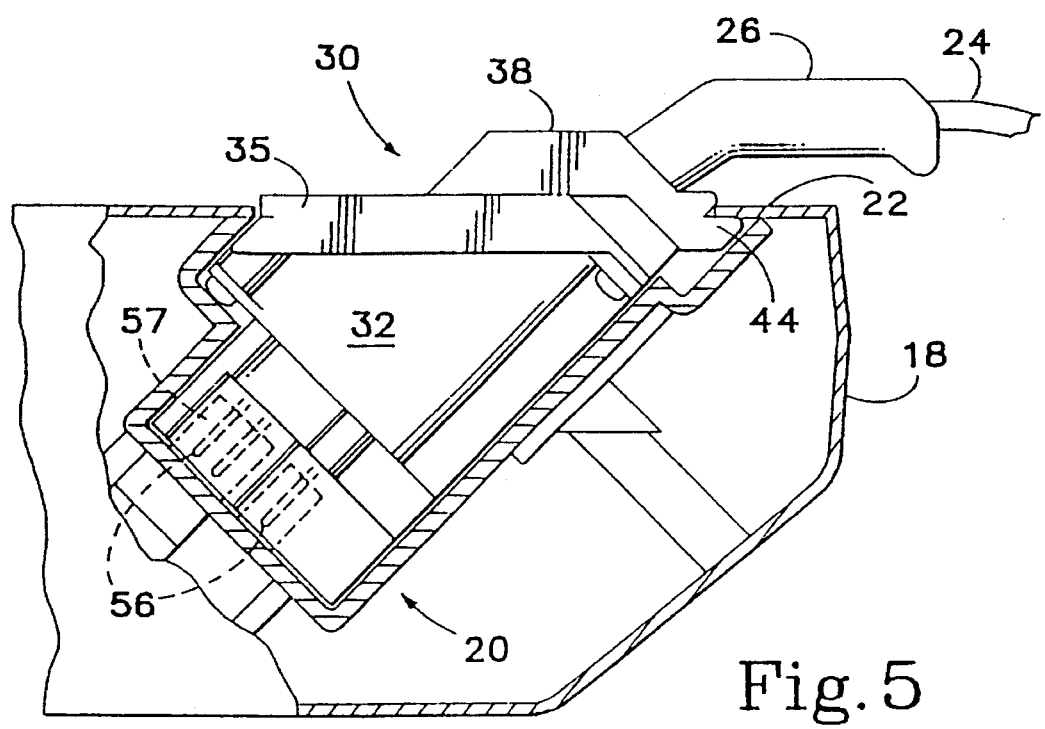
FIG. 5 is an enlarged, partially cutaway view of a plug assembly engaged in a plug connector in the base unit.

FIG. 5 is an enlarged, partially cut-away view showing the plug assembly 30 engaged in a connector assembly 20. Connector assembly 20 is fixed in position within the base unit 18 and arranged to receive any of the plug assemblies 30 (external paddles), 76 (internal paddles), or 116 (patient pads) in interfitting engagement. Plug assembly 30 is shown in FIG. 5 for purposes of illustration. Referring now to FIGS. 2 and 5, plug assembly 30 includes a plug body 32 and a cover 35 coupled to the plug body. A plurality of pins 56 extend from the plug body 32 for electrical connection between the cable assembly and the base unit. Corresponding receptacles 57 are provided in the connector assembly 20 for receiving the pins 56 in an electrical content.

Figure 6:
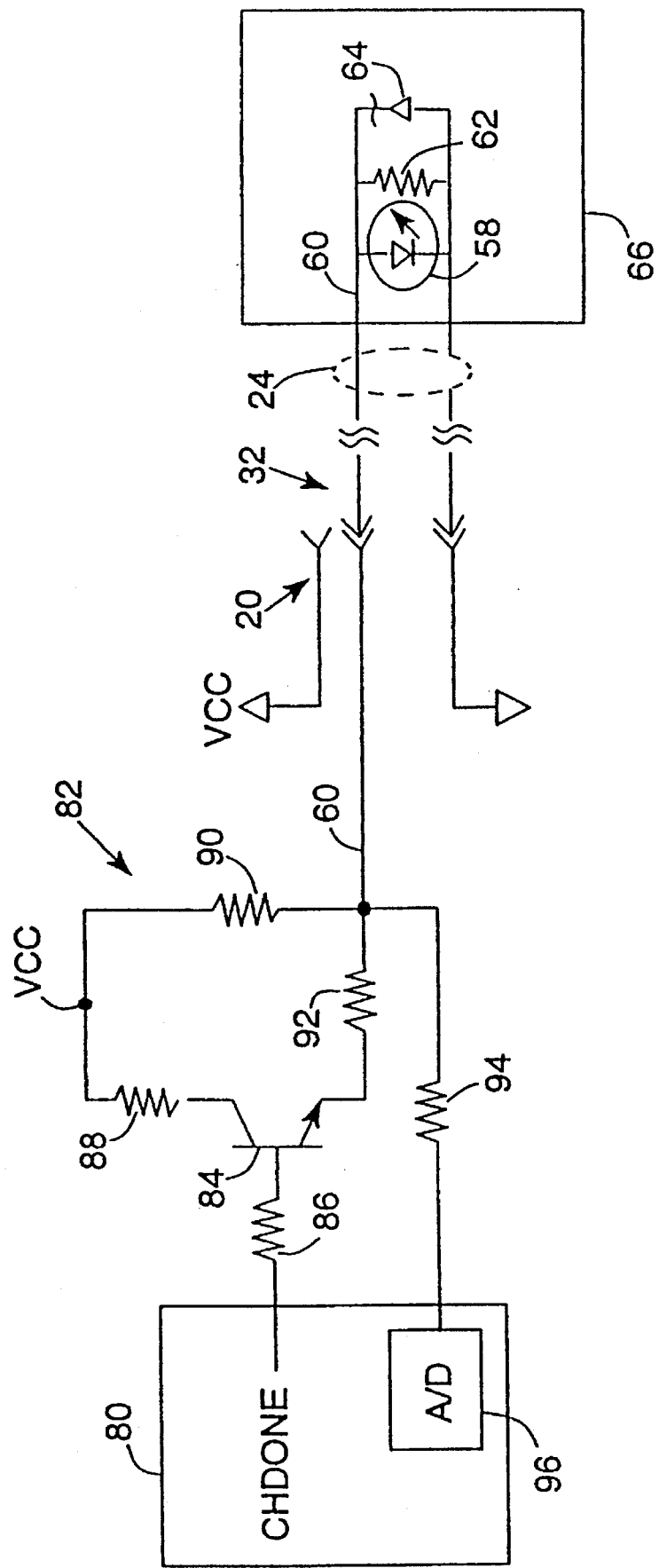
FIG. 6 is an electronic schematic diagram of circuitry for automatically identifying the type of pads or paddles connected to the defibrillator base unit.
Figure 6:
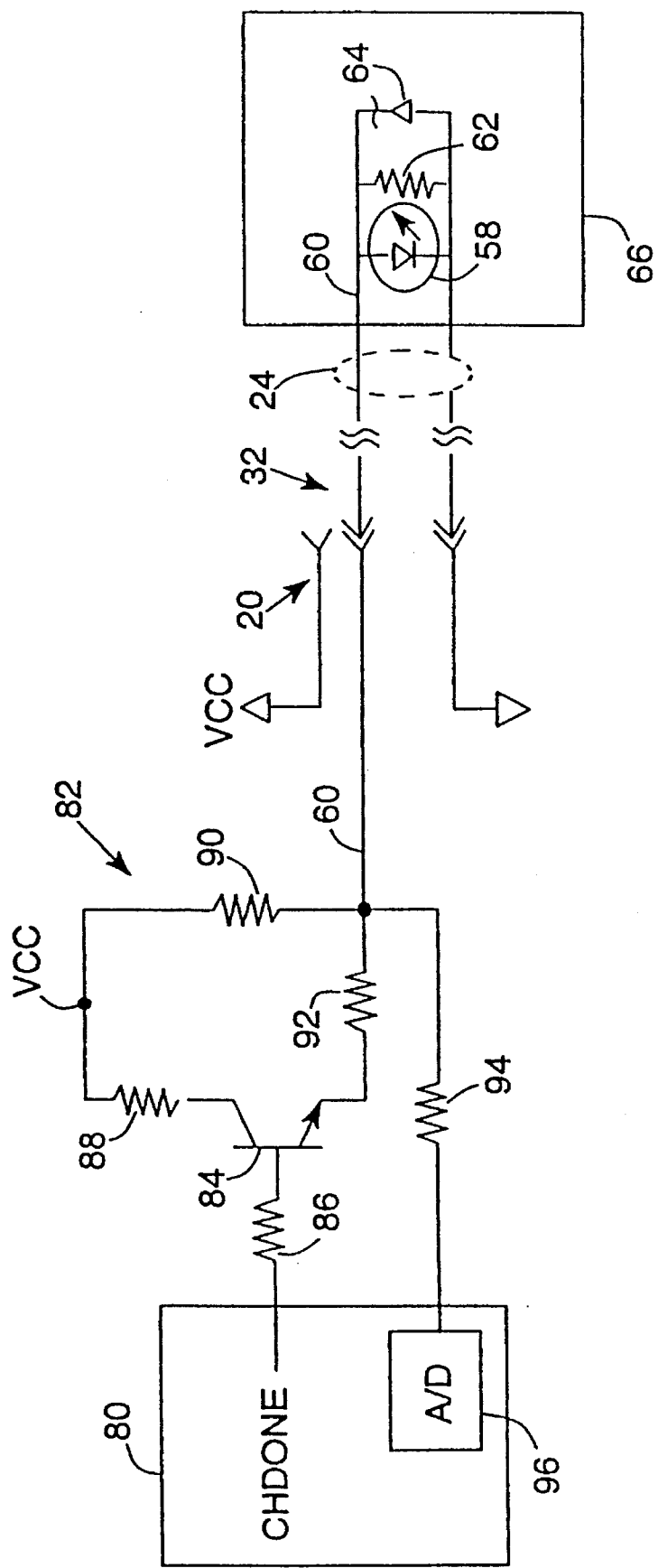

FIG. 6 is a schematic diagram of electronic circuitry used for identifying pads or paddles connected to the base unit. The plug assembly 32 and connector assembly 20 are indicated generally in the center of the drawing, representing the interface between the base unit and the connected pads or paddles. Circuitry shown to the left of connector assembly 20 thus illustrates circuitry disposed within the base unit 18. Circuitry 66, on the right side of the diagram, is electrically coupled through cable 24 to the plug assembly 32.

In the defibrillator base unit, a charge-done driver circuit 82 comprises an NPN transistor 84 which is controlled by a charge-done signal (CHDONE) coupled to the transistor through a base resistor 86. Transistor 84 has a collector terminal coupled through a collector resistor 88 to VCC, which may be, for example, 5 volts DC. The emitter terminal is coupled through an emitter resistor 92 to the charge-done signal line 60. The charge-done signal line 60 is coupled to the connector assembly 20 for connection to any of the various plug assemblies 30, 76 or 116. The charge-done signal line 60 also is coupled through a pull-up resistor 90 to VCC. The charge-done signal line also is coupled through an input resistor 94 to an analog-to-digital conversion circuit 96. The A/D circuit 96 is coupled to or disposed within a defibrillator controller 80 which asserts the charge-done signal when a patient circuit (not shown) is charged to a selected energy level.

Turning now to the right side of FIG. 6, identification circuitry 66 is disposed within the external paddle assembly 40. The external paddle assembly 40 includes a charge-done indicator light 58 (see also FIG. 2), which may be provided by a light emitting diode. A light emitting diode (LED) 58 is disposed between the charge-done signal line 60 and ground line 61. A resistor 62 is disposed in parallel to the LED 58. And finally, a zener diode 64 also is disposed in parallel to LED 58, i.e., between the charge-done signal line 60 and ground connection 61. Only selected signal lines at the defibrillator/plug assembly interface are illustrated in FIG. 6. A more complete list of the defibrillator interface connections is shown in the following table 1:

TABLE 1

PLUG CONNECTOR SIGNALS

| Signal | Definition |
| --- | --- |
| nCHARGE | Apex paddle 40 charge button 67. Charge is asserted low. |
| Charge-done signal 60 | Voltage level indicates the type of paddles connected to the base unit. Also used to light the apex paddle charge done LED 58. |
| VCC | +5VDC |
| PCI | Patient contact impedance. A voltage which turns on a specific number of LEDs on the sternum PCI LED bar (not shown). |
| LOGIC GND | ground |
| nDISCHARGE APEX | A signal asserted when the apex paddle 40 shock button 67 is pressed. |
| nDISCHARGE STERNUM | A signal asserted when the sternum paddle 42 shock button 68 is pressed. |
| HI VOLTAGE APEX | Connects the apex paddle (pad) to the output (−) side of the patient (transfer) circuit and to the pacer (−) terminal (if a pacer is installed). |
| HI VOLTAGE STERNUM | Connects the sternum paddle (pad) to the output (+) side of the patient (transfer) circuit and to the pacer (+) terminal if a pacer is installed. |

In operation, when the patient charging circuit in the defibrillator reaches a selected energy level, the defibrillator controller 80 asserts the charge-done signal CHDONE to turn transistor 84 ON. Transistor 84 drives the charge-done signal line 60 up toward VCC, thereby actuating LED 58 so as to turn on the indicator light, indicating "charge-done" to a user. This occurs only when the external paddles are connected to the base unit, as the other paddles and pads do not have the LED. Nonetheless, the charge-done signal line may be asserted in all cases.

While the charge-done signal is not being asserted by the controller 80, transistor 84 is OFF. During such times, the charge-done signal line 60 essentially is coupled through pull-up resistor 90 to VCC. Referring now to the identification circuit 66 in FIG. 6, the charge-done signal line 60 is coupled through resistor 62 to ground. Resistors 90 and 62 thus form a resistive divider circuit which provides a voltage calculated as follows. If resistor 90 has a value of 10 kΩ and resistor 62 has a value of 2160Ω then the divided value equals 0.178 times 5 volts (VCC) or 0.888 volts. Resistor 62 thus pulls the voltage down to a level which keeps the LED 58 turned off. The voltage at the charge-done signal line 60 is presented through resistor 94 to an analog-to-digital (A/D) converter 96 for sensing the voltage and providing the sensed voltage value to the defibrillator controller 80. The defibrillator controller is arranged to recognize an analog voltage in a range of approximately 0.5 to 3. volts as identifying the external paddles assembly.

In case no pads or paddles are connected to the base unit, resistor 90 pulls the signal line 60 up to approximately VCC or 5 volts. The controller 80 is arranged to recognize a voltage greater than approximately 4 volts as an indication that no pads or paddles are connected to the base unit.

In the case of internal paddles 78, these are connected to the base unit through a plug assembly 76, as noted above. Plug assembly 76 includes means for connecting the single line 60 to ground, thereby driving the signal line 60 to approximately zero volts. Accordingly, the controller 80 is arranged to recognize a voltage of less than approximately 0.5 volts as identifying the internal paddles assembly.

In the case of adhesive patient pads 112, the identifying voltage preferably falls within a range of approximately 3–4 volts DC. Accordingly, a reference voltage circuit which provides a voltage within that range, nominally 3.5 VDC, is disposed in the corresponding plug assembly 116. The voltage reference may be provided by a resistor divider, zener diode, etc. The reference voltage source may be powered by the VCC supply voltage provided to the plug assembly by the base unit. Plug assemblies 76 and 116 thus contain circuitry adequate for identifying the respective pads and paddles by impressing a corresponding voltage onto the charge-done signal line. The identification voltage levels are summarized in the Table 2:

TABLE 2

ANALOG VOLTAGE VALUE vs PADDLES TYPE

| ID VOLTAGE | PADDLES TYPE |
| --- | --- |
| <0.5 V | Internal Paddles |
| ≧0.5, <3 V | External Paddles |
| ≧3.0, <4 V | External Paddles |
| ≧4.0 V | None |

Additional types of pads or paddles may be identified in a similar fashion, by assigning a corresponding identification voltage level (or range) to each such assembly. Even with modest voltage accuracy, say within one-half volt, several more levels could be assigned within the existing 5 volt supply range, by narrowing one or more of the existing ranges set forth in Table 2. Virtually any A/D converter has ample resolution for sensing these levels.

Plug assemblies 76 and 116 each include a pair of discharge switches (not shown) for signalling the defibrillator base unit to deliver a shock to the patient through the connected cable assembly. Both switches must be actuated at the same time to deliver the shock, so as to avoid accidental discharge. The discharge switches are actuated by push buttons 52, 54. Preferably, the discharge switches are mounted on a small circuit board (not shown), disposed inside the plug assembly. Push buttons 52, 54 are exposed through apertures provided in the plug assembly cover 35 for that purpose. The identification circuitry described above conveniently may be disposed in the plug assemblies on the same circuit board as the discharge switches.

Referring now to FIGS. 7–10, the plug assemblies include a latch 38 which is slidably connected to the plug body (for example 34) and extends over at least a portion of the cover 35. The base unit case 18 includes a lip 22 that extends partially over the connector assembly 20 as best seen in cross-section in FIG. 8. Latch 38 includes means 44 defining a recess sized for engaging the lip 22. Latch 38 is slidable between a first or unlocked position as illustrated in FIGS. 7 and 8. When the latch is unlocked, the plug assembly 76 may freely be inserted or removed from the connector assembly 20. In the locked position, as illustrated in FIGS. 9 and 10, means 44 engages the lip 22 so as to prevent removal of the plug assembly from the base unit. Essentially the same latching arrangement is provided in all three illustrated plug assemblies 30, 76, 116.

Plug assemblies 76 and 116, as noted above, include buttons 52, 54 for actuating discharge switches to shock the patient. Referring to FIG. 7, it may be observed that the latch 38, in the unlocked position, partially obscures buttons 52, 54 so as to prevent their actuation by a user. This prevents discharge of the defibrillator unless the plug assembly 76 is securely locked in place in the defibriilator base unit 18. Conversely, as illustrated in FIG. 9, the latch 38, when moved to the lock position, exposes buttons 52 and 54 for use. The latch 38 thus serves the dual purposes of maintaining the plug assembly secured in the base unit and preventing actuation of the discharge switches unless the plug assembly is locked in place.

Having illustrated and described the principles of my invention in a preferred embodiment thereof, it should be readily apparent to those skilled in the art that the invention can be modified in arrangement and detail without departing from such principles. I claim all modifications coming within the spirit and scope of the accompanying claims.

We claim:

1. A defibrillator system comprising:

a defibrillator base unit for providing electrical energy to shock a patient;

means for administering the electrical energy to the patient;

a cable assembly for connecting the administering means to the base unit;

a plug assembly coupled to one end of the cable assembly and arranged for interfitting engagement with the base unit;

a first discharge switch disposed in the plug assembly;

discharge means in the base unit for delivering the electrical energy to the cable assembly to shock the patient in response to actuation of the discharge switch while the plug assembly is connected to the base unit;

means for locking the plug assembly in interfitting engagement with the base unit while in use; and means for preventing actuation of the discharge switch unless the plug assembly is locked in interfitting engagement with the base unit.

2. A defibrillator system according to claim 1 further comprising a second discharge switch disposed in the plug assembly; and wherein the discharge means is arranged to deliver the electrical energy only in response to concurrent actuation of both the first and second discharge switches.

3. A defibrillator system according to claim 2 wherein the preventing means is arranged so that neither of the first and second switches can be actuated unless the plug assembly is locked (FIG. 9) in interfitting engagement with the base unit.

4. A defibrillator system according to claim 1 wherein the plug assembly includes a rigid plug body and the locking means includes a latch slidably coupled to the plug body, the latch being sized and arranged for manual movement between an unlocked position (FIG. 7), in which the latch prevents actuation of the discharge switch, and a locked position (FIG. 9) in which the discharge switch is accessible for actuation by a user.

5. A defibrillator system according to claim 4 further comprising a connector fixed in the base unit for receiving the plug assembly; and wherein the base unit includes a rigid lip extending toward the connector;

the latch includes means for engaging the lip when the plug body is fully engaged in the connector and the latch is moved into the locked position, so that the plug assembly cannot be removed from the base unit.

* * * * *